United States Patent [19]

Moschel et al.

[11] Patent Number: 5,352,669
[45] Date of Patent: Oct. 4, 1994

[54] O[6]-BENZYLATED GUANINE, GUANOSINE AND 2'-DEOXYGUANOSINE COMPOUNDS POSSESSING O[6]-ALKYLGUANINE-DNA ALKYLTRANSFERASE DEPLETING ACTIVITY

[75] Inventors: Robert C. Moschel, Frederick, Md.; M. Eileen Dolan, Chicago, Ill.; Anthony E. Pegg, Hershey, Pa.

[73] Assignee: The of the United States of America as represented by the Department of Health and Human Services, Washington, D.C.

[21] Appl. No.: 616,913

[22] Filed: Nov. 21, 1990

Related U.S. Application Data

[63] Continuation-in-part of Ser. No. 492,468, Mar. 13, 1990, Pat. No. 5,091,430.

[51] Int. Cl.[5] .................. A61K 31/70; A61K 31/52; C07H 17/02; C07D 473/18
[52] U.S. Cl. ...................... 514/45; 514/262; 544/276
[58] Field of Search .......... 544/276; 536/24; 514/45, 262

[56] References Cited

U.S. PATENT DOCUMENTS 4,495,190  1/1985  Hagberg et al. .................. 514/262
4,801,710  1/1989  MacCoss et al. .................. 544/244

OTHER PUBLICATIONS

Harrison's Principles of Internal Medicine, 10th Ed., 1983, pp. 751, 758, 766–775.
Chemical Abstract 104: 199, 241y (1986).
Chemical Abstract 107: 115, 902r (1987).
Chemical Abstract 101: 111, 324g (1984).
Himmelsbach et al., Tetrahedron (1984) 40(1) 59–72.
Chemical Abstract 99 22, 830s (1983).
Trichtinger et al., Tetrahedron Letter (1983) 24(7) 711–714.
Milne et al., J. Med. Chem. (1974) 17(3) 263–268.
Chem. Abstracts, vol. 104:179770s, Karkas et al., J. Med. Chem. 29(5)842–848 (1986).
Chem. Abstr. vol. 100:51936a, Moschel et al., J. Org. Chem. (1984) 49(2) 363–372.
Chem. Abstr. 99:71123x, Ford et al., J. Org. Chem. (1983) 48(13) 226–223.
Chemical Abstr. 71:39386w (1969).
Robins et al., J. Org. Chem. (1969) 34(7) 2160–2163.
Dolan et al, *Cancer Research*, 46, pp. 4500–4505, (1986).
Dolan et al, *Cancer Chemother. Pharmacol.*, 25, pp. 103–108, (1989).
Bowles et al, *J. Med. Chem.*, 6, pp. 471–480 (1963).
Frihart et al. *J. Am. Chem. Soc.*, 95, pp. 7174–7175 (1973).
Pauley et al, *Chem. Res. Toxicol.*, vol. 1, No. 6, pp. 391–397 (1988).

*Primary Examiner*—Robert T. Bond
*Assistant Examiner*—Matthew V. Grumbling
*Attorney, Agent, or Firm*—Birch, Stewart, Kolasch & Birch

[57] ABSTRACT

O[6]-Benzylated guanine guanosine and 2'-deoxyguanosine compounds of the formula

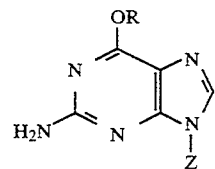

wherein Z is hydrogen,

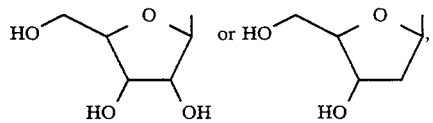

and R is a benzyl group or a substituted benzyl group, cause a depletion of O[6]-alkylguanine-DNA alkyltransferase (AGT) activity in mammalian cells. These compounds may be administered to a host so as to reduce AGT levels in tumor cells of the host in order to increase host responsiveness to anti-neoplastic alkylating agents, including chloroethylating agents, such as chloroethylnitrosoureas, for chemotherapeutic treatment of a number of neoplasms.

10 Claims, 9 Drawing Sheets

$O^6$-BENZYLATED GUANINE, GUANOSINE AND 2'-DEOXYGUANOSINE COMPOUNDS POSSESSING $O^6$-ALKYLGUANINE-DNA ALKYLTRANSFERASE DEPLETING ACTIVITY

BACKGROUND OF THE INVENTION

The present Application is a Continuation-in-Part Application of copending U.S. application Ser. No. 07/492,468, filed on Mar. 13, 1990, which is expressly incorporated by reference herein.

FIELD OF THE INVENTION

The present invention relates to $O^6$-benzylated guanine, guanosine and 2'-deoxyguanosine compounds which possess the ability to deplete $O^6$-alkylguanine-DNA alkyltransferase (AGT) activity in vivo, and to methods for the administration thereof to enhance chemotherapeutic treatment of tumor cells. More specifically, the present invention relates to $O^6$-benzylguanine, $O^6$-benzylguanosine, $O^6$-benzyl-2'-deoxyguanosine and related $O^6$-benzylated derivatives wherein the benzyl groups thereof may be substituted at the ortho, meta or para position. The present invention also relates to methods for administering compositions containing these compounds to a host in order to reduce the activity of AGT in tumor cells of the host which increases host responsiveness to anti-neoplastic alkylating agents such as streptozotocin, procarbazine or dacarbazine as well as to chloroethylating agents, such as chloroethyl-nitrosoureas or chloroethyl triazenes, subsequently or simultaneously administered to the host.

DESCRIPTION OF RELATED ART

Chemotherapeutic chloroethylating agents have some clinical utility against a number of neoplasms but in general have only limited effectiveness in killing tumor cells. The marginal usefulness of these agents may be explained on a cellular level by the local concentration of DNA repair proteins present in the tumor. There is strong evidence that the repair protein $O^6$-alkylguanine-DNA alkyltransferase (AGT) present to some degree in all mammalian tumors studied to date, is responsible for protecting cells from the antitumor effects of chloroethylating agents such as chloroethylni-trosoureas. The AGT acts to remove the initial DNA adduct formed at the $O^6$-position of guanine by these agents before this adduct can be converted to a lethal lesion. Efforts to reduce the level of AGT in order to increase the sensitivity of cells to the chemotherapeutic effects of chloroethylating or other alkylating agents would be advantageous to therapy which involves cytotoxic lesions at the $O^6$-position of guanine. Furthermore, a specific decrease in AGT levels allows one to study the biological effects of alkylating agents.

Previous studies have indicated that the chemotherapeutic effectiveness of chloroethylating and methylating agents can be enhanced in human cells in culture by pretreatment with $O^6$-alkylguanines. Earlier investigations demonstrated that agents such as $O^6$-methyl-and $O^6$-n-butylguanine decreased AGT levels in human tumor cells in culture which led to an enhancement in the sensitivity of these cells to the cytotoxic effects of chloroethylating agents (Dolan et al, Cancer Research, 46, pp. 4500–4504, (1986)). Subsequent studies demonstrated that there was a dose dependent decrease in AGT levels in human colon xenograft tumors carried in nude mice after intraperitoneal injections of $O^6$-methyl-guanine (Dolan et al, Cancer Chemother. Pharmacol., 25, pp. 103–108, (1989)). However, these compounds were not potent enough to be likely to be useful for treatment of patients since the rate of AGT depletion was slow and the extent of depletion was not complete even with very high doses.

$O^6$-benzylguanine differs from $O^6$-methyl- and $O^6$-n-butylguanine in that the alkyl substituent is replaced with a benzyl group and it is a known intermediate compound. See Bowles et al, J. Med. Chem., 6, pp. 471–480 (1963); Frihart et al, J. Am. Chem. Soc., 95, pp. 7174–7175 (1973). However, the use of this compound in chemotherapeutic treatment has yet to be reported.

$O^6$-Benzylguanine is a known intermediate compound, the synthesis of which was reported for example by Bowles et al., J. Med. Chem., 6, pp 471–480 (1963).

Pauly et al., in Chem. Res. Toxicol., Vol. 1, No. 6, pp. 391–397 (1988), synthesized abbreviated rodent H-ras DNA sequences which were modified to contain $O^6$-substituted 2'-deoxyguanosine residues at the first, second or both positions of Codon 12. A synthesis method for $O^6$-benzyl-2'-deoxyguanosine is reported in the Pauly et al. reference.

SUMMARY OF THE INVENTION

Therefore, it is an object of the present invention to provide novel compounds useful for effectively reducing AGT levels in tumor cells.

Another object of the present invention is to provide pharmaceutical compositions containing compounds which effectively reduce AGT levels in cells.

Yet a further object of the present invention is to provide methods for depleting AGT levels in tumor cells.

Still another object of the present invention is to provide methods for increasing host responsiveness to anti-neoplastic chloroethylating agents or other alkylating agents by administering to the host compositions containing compounds which deplete AGT levels in the tumor cells in the host.

The foregoing objects and others are accomplished in accordance with the present invention by providing compositions containing $O^6$-benzylated guanine derivative of the following formula (I):

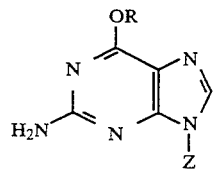

formula (I)

wherein Z is hydrogen,

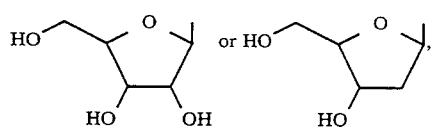

and R is a benzyl group or a benzyl group substituted at the ortho, meta or para position with a substituent group such as halogen, nitro, aryl such as phenyl or substituted phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, and $SO_nR_1$ wherein n is 0, 1, 2 or 3 and $R_1$ is hydrogen alkyl of 1–4 carbon atoms or aryl; and a pharmaceutically acceptable excipient. R is preferably a benzyl group or a benzyl group substituted with a substituent group such as halogen, nitro, alkyl of 1–4 carbon atoms, alkoxy of 1–4 carbon atoms, trifluoromethyl and hydroxymethyl. In an alternative embodiment, this composition may further include an anti-neoplastic alkylating agent, such as a chloroethylating agent.

In another embodiment of the present invention, a method is provided for depleting the activity of $O^6$-alkylguanine-DNA alkyltransferase (AGT) in tumor cells which comprises administering to a host compositions containing compounds of formula (I) and a pharmaceutically acceptable excipient. In a further embodiment of the present invention, a method is provided for increasing host responsiveness to anti-neoplastic chloroethylating or other alkylating agents by administering to the host compositions containing compounds of formula (I) and a pharmaceutically acceptable excipient and subsequently or simultaneously administering the anti-neoplastic chloroethylating or alkylating agents.

In yet a further embodiment of the present invention, novel compounds are provided having the chemical structure of formula (I) above, wherein R is a benzyl group substituted at the ortho, meta or para position with a substituent group such as halogen, nitro, aryl such as phenyl or substituted phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, and $SO_nR_1$ wherein n is 0, 1, 2 or 3 and $R_1$ is hydrogen, alkyl of 1–4 carbon atoms or aryl.

In the novel compounds encompassed herein, Z is preferably hydrogen and R is preferably a benzyl group substituted with a substituent group such as halogen, nitro, alkyl of 1–4 carbon atoms, alkoxy of 1–4 carbon atoms, trifluoromethyl and hydroxymethyl.

Further scope of the applicability of the present invention will become apparent from the detailed description and drawings provided below. However, it should be understood that the detailed description and specific examples while indicating preferred embodiments of the invention are given by way of illustration only since various changes and modifications within the spirit and scope of the invention will become apparent to those skilled in the art from this detailed description.

BRIEF DESCRIPTION OF THE DRAWINGS

The invention is further illustrated in the accompanying drawings wherein.

DETAILED DESCRIPTION OF THE INVENTION

Figure 1:
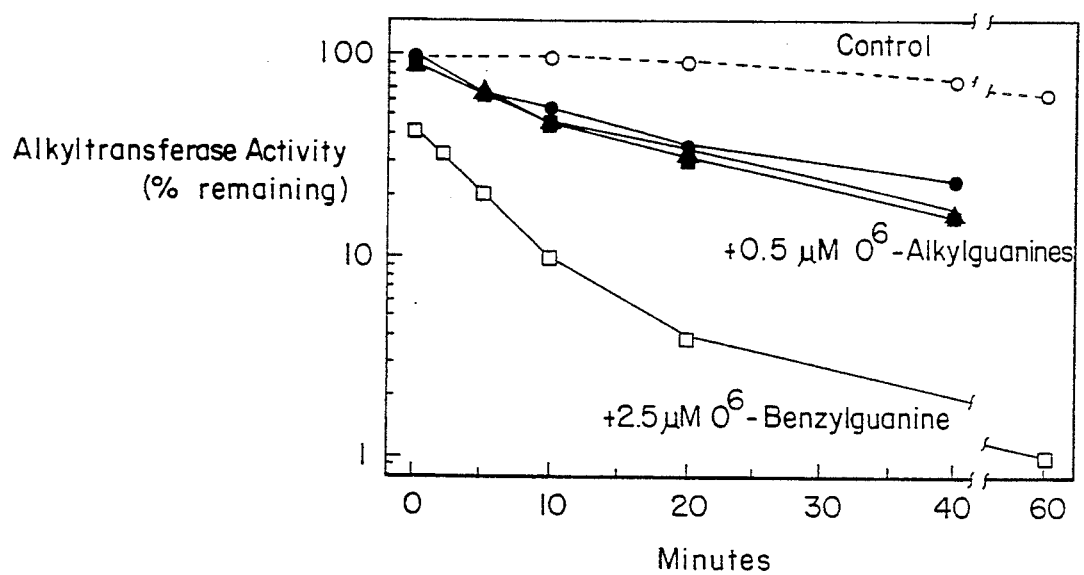
FIG. 1 is a graph showing the rate of inactivation of human alkyltransferase by $O^6$-benzylguanine and related compounds.

Compounds encompassed by and useful in the present invention include compounds of the following formula (I):

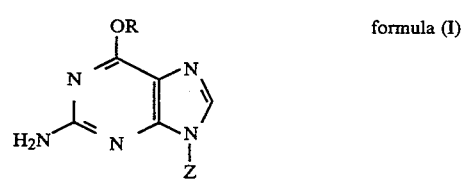

formula (I)

wherein Z is hydrogen,

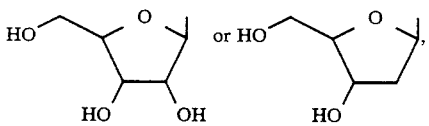

and R is a benzyl group or a benzyl group substituted at the ortho, meta or para position with a substituent group such as halogen, nitro, aryl such as phenyl or substituted phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, $SO_nR_1$ where n is 0, 1, 2 or 3 and $R_1$ is hydrogen, alkyl of 1–4 carbon atoms or aryl. Z is preferably hydrogen, and R is preferably a benzyl group or a benzyl group substituted with a substituent group such as halogen, nitro, alkyl of 1–4 carbon atoms, alkoxy of 1–4 carbon atoms, trifluoromethyl and hydroxymethyl. Examples of such compounds include $O^6$-(p-chlorobenzyl)guanine, $O^6$-(p-fluorobenzyl)guanine, $O^6$-(p-methylbenzyl)guanine, $O^6$-benzylguanosine and $O^6$-benzyl-2'-deoxyguanosine. All such $O^6$-benzylated compounds would be expected to exhibit AGT depletion characteristics and can be synthesized using appropriate adaptions known to those skilled in the art of the general description presented below.

$O^6$-Benzylguanine is a known intermediate compound which may be conventionally prepared as disclosed in Bowles et al, *J. Med. Chem.*, 6, pp. 471–480 (1963) and Frihart et al, *J. Am. Chem. Soc.*, 95, pp. 7144–7175 (1973).

$O^6$-Benzylguanines substituted on the benzyl group at either the ortho, meta or para position may be synthesized by treating 2-amino-6-chloropurine with the alkoxide of a benzyl alcohol bearing the desired ortho, meta or para substituent. For example, $O^6$-(p-chlorobenzyl)guanine and $O^6$-(p-methylbenzyl)guanine may be prepared by treating 2-amino-6-chloropurine with an appropriate amount of sodium 4-chlorobenzyloxide in 4-chlorobenzyl alcohol or sodium 4-methylbenzyloxide in 4-methylbenzyl alcohol, respectively, followed by precipitation and purification of the product. Ortho and meta substituted products can be prepared in the analogous fashion.

The synthesis of $O^6$-benzyl-2'-deoxyguanosine is reported by Pauly et al., *Chem. Res. Toxicol.*, Vol. 1, No. 6, pp. 391–397 (1988). The synthesis method reported is similar to that provided by Gaffney and Jones, *Tetrahedron Lett.*, Vol. 23, 2253–2256 (1982) for providing $O^6$-alkyl derivatives of 2'-deoxyguanosine. Other $O^6$-substituted benzyl derivatives of 2'-deoxyguanosine encompassed hereby may also be prepared using synthesis techniques similar to or analogous to those disclosed by Pauly et al. Moreover, the benzyl and substituted benzyl derivatives of guanosine encompassed hereby also can be prepared using techniques similar or analogous to those disclosed by Pauly et al. and/or Gaffney and Jones, if desired. Both the Pauly et al. and Gaffney and Jones references are expressly incorporated by reference herein.

The methods of the present invention include the administration of the above-noted compositions containing the compounds of formula (I) and a pharmaceutically acceptable excipient to a host.

In the methods according to the present invention, pharmaceutical compositions containing compounds according to the present invention are administered in an effective amount to a host so as to deplete AGT levels in tumor cells in the host thereby increasing host responsiveness to anti-neoplastic chloroethylating agents or other alkylating agents, so that subsequent or simultaneous administration of these anti-neoplastic agents to the host results in effective chemotherapeutic treatment for killing tumor cells.

The $O^6$-substituted guanine, 2'-deoxyguanosine and guanosine compound containing compositions in accordance with the present invention may be used to reduce AGT levels in the treatment of various neoplasms, such as brain tumors, lymphomas, leukemias and solid tumors.

EXAMPLES

Analytical Methods. Proton nuclear magnetic resonance ($^1$H-NMR) spectra were recorded on a Varian XL 200 instrument interfaced to an Advanced data system. Samples were dissolved in dimethyl-$d_6$ sulfoxide with tetramethylsilane as internal standard. Positive ion (+ve) fast atom bombardment (FAB) mass spectra (MS) were obtained with a reversed geometry VG Micromass ZAB-2F spectrometer interfaced to a VG 2035 data system. A mixture of dithiothreitol and dithioerythritol (1:1) was used as FAB matrix.

Chemicals and Drugs. Chemotherapeutic agents 1-(2-chloroethyl)-3-cyclohexyl-1-nitrosourea (CCNU) (NSC 79037) and 2-chloroethyl(methylsulfonyl)methanesulfonate (Clomesone) (NSC 33847) were obtained from the Drug Synthesis and Chemistry Branch, Division of Cancer Treatment, National Cancer Institute, Bethesda, Md. [$^3$H]-Methylnitrosourea (5.6 Ci/mmol) was purchased from Amersham. All other chemicals were purchased from Fisher, Calbiochem, Sigma or Aldrich.

$O^6$-Benzylguanine, $O^6$-(p-chlorobenzyl)guanine and $O^6$-(p-methylbenzyl)guanine were prepared by treating 2-amino-6-chloropurine (0.018 mol) with 2.2 equivalents of either sodium benzyloxide, sodium 4-chlorobenzyloxide, or sodium 4-methylbenzyloxide in 30g of either benzyl, 4-chlorobenzyl or 4-methylbenzyl alcohol, respectively at 130° C. for 6h. The resulting suspensions were cooled to room temperature, treated with 2.5 ml glacial acetic acid with stirring and then poured into 1 liter of diethyl ether with vigorous stirring. The precipitated solids were collected by filtration and were crystallized from either $H_2O$ or ethanol/$H_2O$ (4:5) with decolorizing carbon as necessary to afford 50% yields of the respective $O^6$-benzylated guanine. $O^6$-(p-Chlorobenzyl)guanine; UV, $\lambda_{max}$ (pH7) 239, 283; $^1$H-NMR, Δ5.48 (s,2,ArCH$_2$) , 6.29(br s,2,NH$_2$, exchange with D$_2$O) , 7.50(dd,4,Ar) , 7.83(s,1,8−H) , 12.43(br s,1,9-H, exchanges with D$_2$O); +ve FAB MS, m/z 276 ([M+H]+), 152([Guanine+H]+), 125([C$_7$H$_6$Cl]+). Anal. Clcd. for C$_{12}$H$_{10}$N$_5$OCl 1/2H$_2$O: C,50.62; H,3.89; N,24.60. Found: C,51.02; H,3.82; N,25.15. $O^6$-(p-Methylbenzyl)guanine: UV, $\lambda_{max}$ (pH 7) 241,283; $^1$H-NMR, Δ2.31 (s,3,ArCH$_3$), 5.43 (s,2,ArCH$_2$), 6.28(br s,2,NH$_2$) 7.30(dd,4,Ar) , 7.80(s,1,8-H) , 12.41(br s,1,9-H, exchanges with D$_2$O); +ve FAB MS, m/z 256( [M+H]+) , 152 ([Guanine+H]+) , 105 ( [C$_8$H$_9$]+) . Anal. Calcd. for C$_{13}$H$_{13}$N$_5$O: C,61.17; H,5.13; N,27.43. Found: C,61.05; H,5.13; N,27.14.

$O^6$-(p-Fluorobenzyl)guanine was prepared in a fashion similar to that of the above compound.

$O^6$-benzyl-2'-deoxyguanosine was prepared in a fashion similar to that taught by Pauly et al. (*Chem. Res. Toxicol.*, Vol. 1., No. 6, pp. 391–397 (1988)).

Cell Culture. The human colon carcinoma line HT29 was maintained in Dulbecco's modified Eagles medium containing 36 mM NaHCO$_3$ supplemented with 10% fetal bovine serum, gentamycin (50 ug/ml) and 3% glutamine in a humidified atmosphere of 5% CO$_2$ at 37° C. Cells were seeded weekly at $2.5 \times 10^5$ cells/75 cm$^2$ flask.

Three days prior to treatment, HT29 cells were plated at a density of $5 \times 10^6$ cells/150 cm$^2$ flask. After growth for 2–3 days, the medium on cells was replaced with fresh medium or medium containing $O^6$-alkylguanine derivatives. The treatment conditions such as concentration and time of exposure are indicated below in Examples 1–4. The cells were then harvested, collected by centrifugation at $1000 \times g$ in medium, washed with ice-cold phosphate buffered saline and the cell pellets stored at $-80°$ C. until assaying for alkyltransferase. Extracts were conventionally prepared as described previously in Domoradski et al, *Carcinogenesis*, 5, pp. 1641–1647 (1984).

Cell colony forming efficiency was determined by plating HT29 cells at a density of $1 \times 10^6$ cells/25 cm$^2$ flask 24 hours (h) prior to replacing medium with fresh medium or medium containing 10 uM $O^6$-benzylguanine for 2h. Cells were then treated with various concentrations of chloroethylating agent for 2h at 37° C. The medium was then replaced with the same medium as that used for the pretreatment for an additional 18h, and the cells were replated at densities between 100 and 3200 per 25 cm$^2$ flask. The cells were allowed to grow for 10–12 days and colonies were then washed with 0.9% saline, stained with 0.5% crystal violet in ethanol and counted.

EXAMPLE 1

The rate of inactivation of human alkyltransferase by $O^6$-benzylguanine and related compounds was measured and the results are shown in FIG. 1. The alkyltransferase from HT29 cells was incubated without addition (○) or with 2.5 uM $O^6$-benzylguanine (□), 0.5 uM of $O^6$-benzylguanine (■), 0.5 uM of $O^6$-(p-chlorobenzyl)guanine (▲) or with 0.5 uM of $O^6$-(p-methylbenzyl)guanine (●) in a total volume of 0.99 ml for the time shown and then the residual alkyltransferase activity was determined by addition of 0.01 ml containing the $^3$H-methylated DNA substrate for 30 min. The alkyltransferase activity was then determined and expressed as the percentage remaining based on that present in untreated controls (approximately 804 fmol/mg protein).

EXAMPLE 2

Figure 2A:
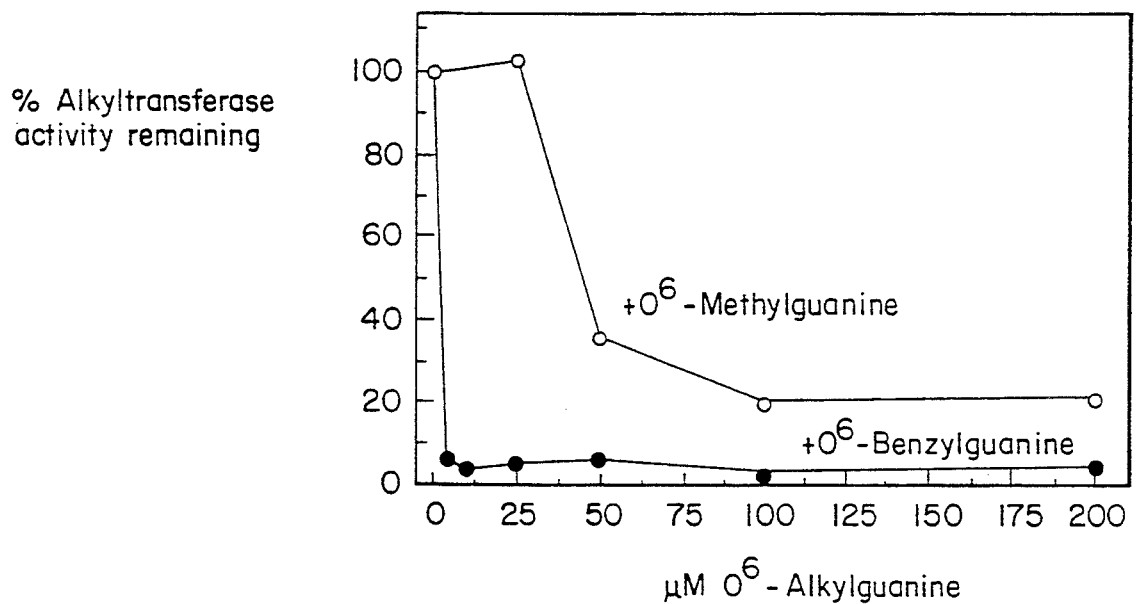
FIGS. 2(A) and 2(B) are graphs showing the loss of alkyltransferase activity in HT29 cells exposed to $O^6$-benzylguanine.
Figure 2B:
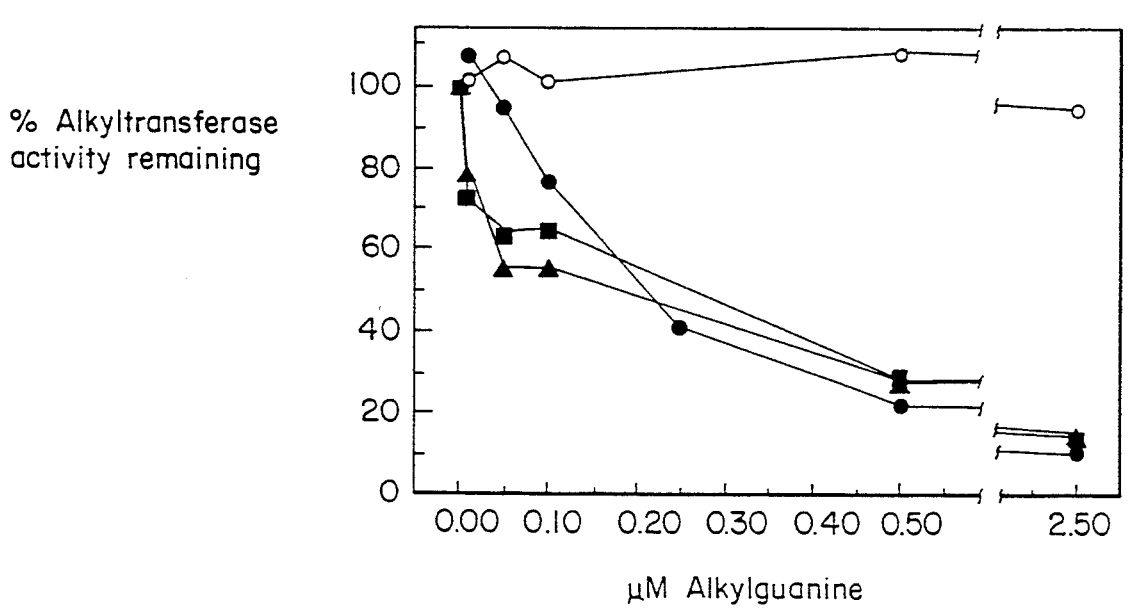

The loss of alkyltransferase activity in HT29 cells exposed to $O^6$-benzylguanine was measured and the results are shown in FIGS. 2(A) and 2(B). In the experiment shown in FIG. 2(A) the cells were exposed to $O^6$-benzylguanine or $O^6$-methylguanine at concentrations of 5 to 200 uM as shown for 4h. In the experiment shown in FIG. 2(B), the cells were exposed to $O^6$-benzylguanine (●), $O^6$-(p-chlorobenzyl)guanine (■), $O^6$-(p-methylbenzyl)guanine (▲) or 7-benzylguanine (○) at concentrations of 0.01 to 2.5 uM for 4h.

EXAMPLE 3

Figure 3:
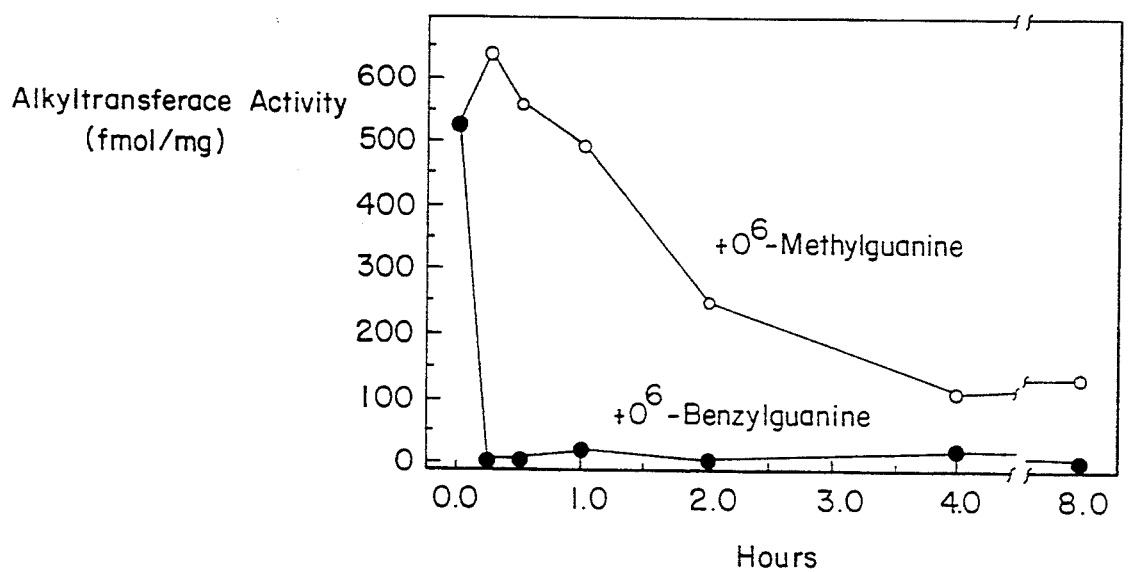
FIG. 3 is a graph showing the time course of the loss of alkyltransferase activity in HT29 cells.

A graph of a time course of the loss of alkyltransferase activity in HT29 cells is shown in FIG. 3. The cells were exposed to 100 uM $O^6$-benzylguanine or $O^6$-methylguanine for the time indicated, then rinsed with PBS and extracts prepared for alkyltransferase analysis.

EXAMPLE 4

Figure 4A:
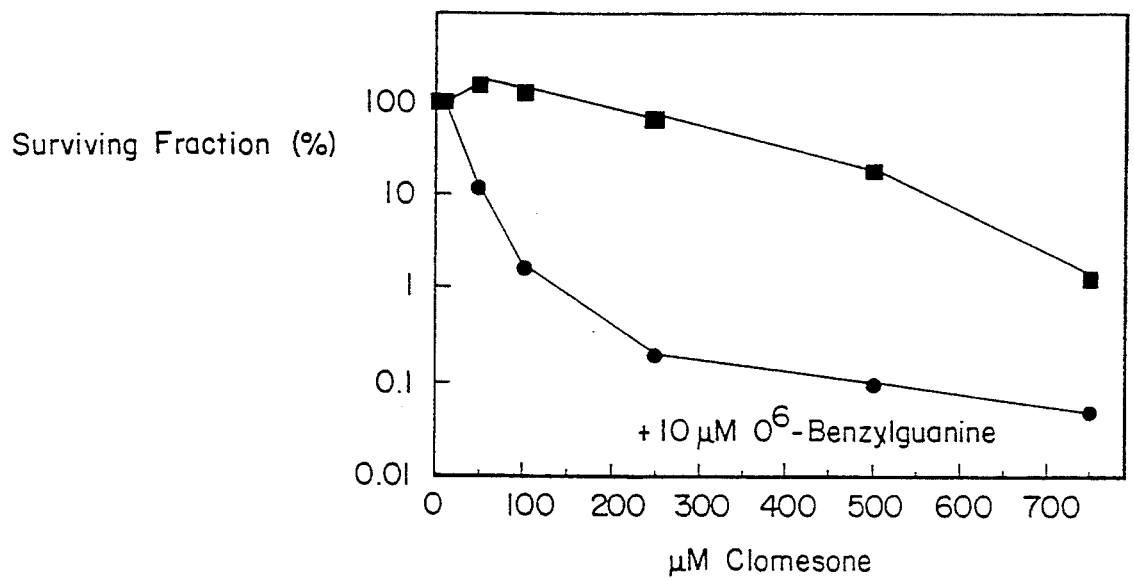
FIGS. 4(A) and 4(B) are graphs showing the enhancement of cytotoxicity of chloroethylating agents by $O^6$-benzylguanine.
Figure 4B:
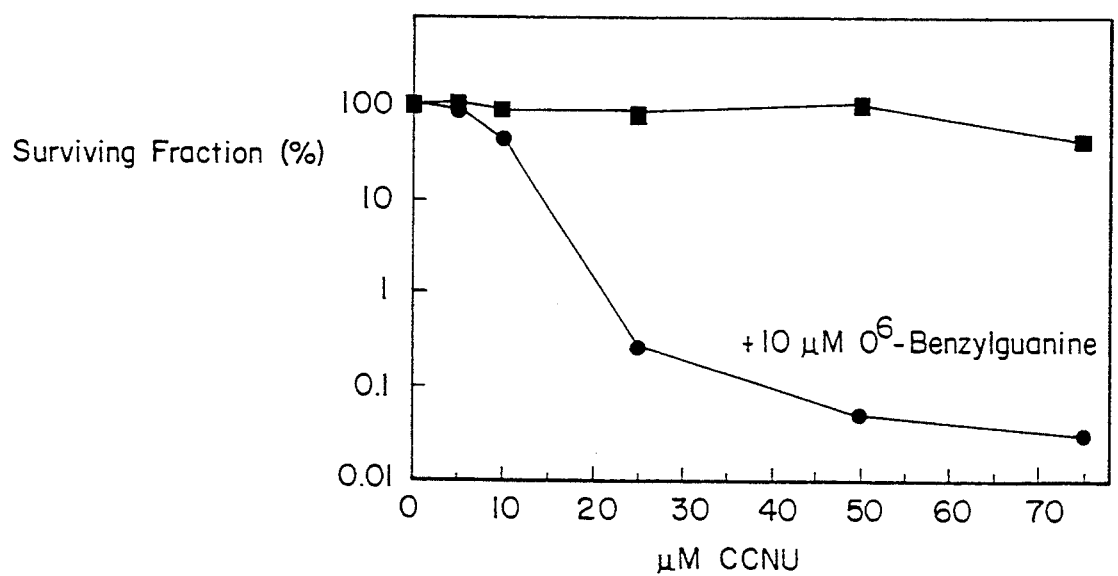

The enhancement of cytotoxicity of chloroethylating agents by $O^6$-benzylguanine was measured and the results are shown in FIGS. 4(A) and 4(B). Cultures of HT29 cells were exposed to fresh medium or medium containing 10 uM $O^6$-benzylguanine for 2h and then both sets were treated with the concentration shown of CCNU (FIG. 4(A)) or Clomesone (FIG. 4(B)) for 2h. Colony forming efficiency determined as described under Materials and Methods is expressed as % survival (relative to zero drug addition).

Animal Treatment. Male CD-1 mice (approx. 37g) were purchased from Charles River Breeding Laboratories, Inc. (Wilmington, Del.). Animals were treated with $O^6$-benzylguanine at a dose of 10.2 mg/kg body weight by intraperitoneal injection. The treatment consisted of injection of approximately 1 ml of a solution of 0.2 mg/ml of $O^6$-benzylguanine in 0.9% saline at zero time followed by a second injection one hour later. In a separate experiment, mice were treated at a dose of 126 mg/kg by injection of about 1 ml of a solution of 5 mg $O^6$-benzylguanine in 1 ml of 10% cremophor EL (Sigma) in 0.9% saline, pH 7.0. Control animals received the vehicle alone. Animals were sacrificed by cervical dislocation at various time periods, tissues were removed and frozen at -80° C until analysis. Crude extracts from tissues for alkyltransferase assay were conventionally prepared as described previously in Pegg et al, *J. Biol. Chem.*, 258, PP. 2327–2333 (1983). Further treatment conditions are described below in Example 5.

EXAMPLE 5

Figure 5:
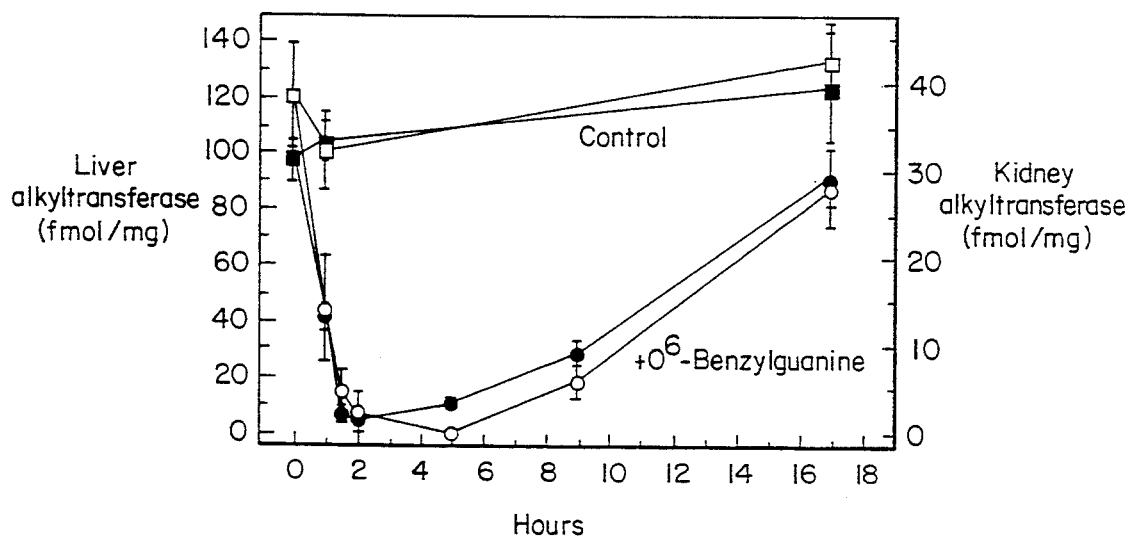
FIG. 5 is a graph showing the depletion of alkyltransferase in mouse tissues by administration of $O^6$-benzylguanine.

The depletion of alkyltransferase in mouse tissues by administration of $O^6$-benzylguanine was measured and the results are shown in FIG. 5. CD-1 mice (body wt. about 37g) were given an intraperitoneal injection of 1 ml of saline containing 0.2 mg of $O^6$-benzylguanine (●,○) or 1 ml of saline alone (■,□) at zero time and at one h. The mice were killed at the time shown and the alkyltransferase activity was determined in liver (●, ■) or kidney (○, □) extracts. The means±S.D. for estimations on three mice which were each assayed in duplicate are shown.

Alkyltransferase assay and inactivation. Extracts containing alkyltransferase were incubated with various concentrations of $O^6$-benzylguanine or $O^6$-methylguanine as indicated. The possible reversal of inactivation was investigated by dialysis against 50 mM Tris, 0.1 mM EDTA and 5 mM dithiothreitol for 16h following incubation of 25 uM $O^6$-benzylguanine in HT29 extract for 2h at 37° C. Alkyltransferase activity was measured as removal of $O^6$-[$^3$H]methylguanine from a [$^3$H]methylated DNA substrate which was prepared by reacting [$^3$H]methylnitrosourea with DNA at 37° C. for 30 min. The DNA was precipitated by adding ice-cold perchloric acid at a final concentration of 0.25N and hydrolyzed in 0.1 N HCl at 70° C. for 30 min as described in Domoradski (1984), supra. The modified bases were separated by conventional reverse-phase HPLC as described in Dolan et al (1986), supra. Protein was determined by the conventional method of Bradford (*Anal. Biochem.*, 72, pp. 248–254 (1976)) and the results expressed as fmol of $O^6$-methylguanine released from the DNA per mg of protein.

RESULTS

As shown in Table 1, in vitro exposure of the human $O^6$-alkylguanine-DNA alkyltransferase to 0.25 uM $O^6$-benzylguanine for 30 min led to a loss of more than 50% of the alkyltransferase activity and exposure to 2.5 uM or higher concentrations completely inactivated the protein.

TABLE 1

Loss of alkyltransferase activity in response to exposure to $O^6$-benzylguanine and related compounds

| Treatment | % alkyltransferase remaining |
|---|---|
| 0.25 uM $O^6$-benzylguanine, 30 min | 45 |
| 0.25 uM $O^6$-(p-chlorobenzyl) guanine, 30 min | 45 |
| 0.25 uM $O^6$-(p-methylbenzyl) guanine, 30 min | 44 |
| 2.5 uM $O^6$-benzylguanine, 30 min | 3 |
| 5 uM $O^6$-benzylguanine, 30 min | <1 |
| 5 uM 7-benzylguanine, 30 min | 100 |
| 25 uM $O^6$-methylguanine, 60 min | 95 |
| 200 uM $O^6$-methylguanine, 60 min | 44 |
| 5 uM $O^6$-benzylguanine, 60 min | <1 |
| 5 uM $O^6$-benzylguanine, 60 min, followed by dialysis for 16 h at 4° C. | <1 |

The loss of alkyltransferase activity was irreversible. Dialysis for 16h at 4° C. of extracts inactivated by reaction with 25 uM $O^6$-benzylguanine led to no restoration of activity. The related compounds, $O^6$-(p-chlorobenzyl)guanine or $O^6$-(p-methylbenzyl)guanine, were as active in reducing alkyltransferase as $O^6$-benzylguanine itself but 7-benzylguanine had no inhibitory effect and, in agreement with previous reports (Dolan et al, *Cancer Res.*, 45, pp. 6413–6417 (1985); Yarosh et al, *Cancer Res.*, 46, pp. 1663–1668 (1986), $O^6$-methylguanine was only weakly active requiring 200 uM concentrations for 60 min to reduce activity by about 50% as shown in Table 1. Inactivation of the alkyltransferase by $O^6$-benzylguanine and the para-substituted analogues was rapid with 50% of the activity lost within 10 min of exposure to 0.5 uM and 90% of the activity lost within 10 min of incubation with 2.5 uM solutions (FIG. 1). It can also be seen in FIG. 1 that the presence of 2.5 uM $O^6$-benzylguanine in the assay medium decreased the measured alkyltransferase activity by 57%. This inhibition which occurred in the absence of any preincubation of the alkyltransferase with the drug indicates that $O^6$-benzylguanine is an effective competitive inhibitor with respect to the methylated DNA substrate.

Exposure of HT29 cells to $O^6$-benzylguanine led to the efficient depletion of alkyltransferase activity (FIGS. 2(A) and 2(B)). Complete loss of activity was seen in response to addition of 5 uM or higher concentrations of this compound to the culture medium for 4h while 100 uM concentrations of $O^6$-methylguanine were needed to achieve a maximal response which was only an 80% reduction in activity (FIG. 2(A)). As illustrated in FIG. 2(B), the depletion was dose dependent in the range of 0 to 2.5 uM for the three $O^6$-benzylguanine derivatives while 7-benzylguanine exhibited no effect. This latter observation together with the data in Table 1 establishes that the inhibitory effect of the $O^6$-benzylguanines is the result of the attachment of the respective benzyl group to the $O^6$-position of the purine and is not a general result of exposure to any benzylated guanine.

The data of FIG. 2(B) also indicates that at very low concentrations (i.e. 10 to 100 nM) the p-chlorobenzyl and p-methylbenzyl-derivatives were somewhat more potent than $O^6$-benzylguanine but at doses of 0.5 uM or higher all three compounds were equally active.

The time course for alkyltransferase depletion in HT29 cells by both $O^6$-benzylguanine and $O^6$-methylguanine is illustrated in FIG. 3. The presence of $O^6$-benzylguanine at 100 uM concentration in the culture medium caused a complete loss of alkyltransferase activity within 15 min and this was maintained over the entire 8h period studied. The identical exposure to $O^6$-methylguanine produced only an 80% reduction and the maximal effect required 4h of exposure (FIG. 3). The rate of recovery of alkyltransferase activity was analyzed in HT29 cells by changing the medium to remove the base after exposure to 10 uM $O^6$-benzylguanine or 400 uM $O^6$-methylguanine for 2h. The alkyltransferase activity remained below 4% of control values for up to 8h after the period of exposure to $O^6$-benzylguanine. In contrast, as previously reported (Dolan et al (1985), supra; Dolan et al, *Cancer Res.*, 48, pp. 3603–3606 (1988)), after the same time of exposure to $O^6$-methylguanine there was a steady rise in alkyltransferase activity which reached 34% at 8h.

The reduction of alkyltransferase in HT29 cells by exposure to 10 uM $O^6$-benzylguanine for 2h led to a very marked increase in the cytotoxicity of either CCNU (FIG. 4(A)) or Clomesone (FIG. 4(B)). Exposure to $O^6$-benzylguanine alone showed no toxic effects at doses below 100 uM for 24h.

In addition to the above tests on the ability of compounds of Formula I to reduce alkyltransferase activity in HT29 cells, a second set of Experiments with $O^6$-benzylguanine $O^6$-(p-fluorobenzyl)guanine and $O^6$-benzyl-2'-deoxyguanosine were also performed. These additional experiments were performed utilizing techniques such as described above. Each of the compounds shown in Table II were able to reduce alkyltransferase activity when they were tested.

TABLE 2*

| Drug Concentration (μM) | $O^6$-benzyl-guanine | $O^6$-(p-fluoro-benzyl) guanine | $O^6$-benzyl-2'-deoxy-guanosine |
|---|---|---|---|
| 0 | 100 | 100 | 100 |
| 0.05 | 96 | 43 | 57 |
| 0.1 | 70 | 49 | 65 |
| 0.5 | 39 | 10 | 44 |
| 5 | 7 | 5 | 2 |
| 25 | 5 | 9 | 3 |
| 100 | 3 | 2 | 2 |

*HT29 cells were exposed to the drugs at the indicated concentrations for 4h. Cells were then rinsed with phosphate buffered saline solution and extracts were prepared for alkyltransferase analysis. The results are expressed as percentage of the alkyltransferase activity present at the time of addition of the drugs and indicate at least one experiment with duplicate estimations.

In order to be a clinically or experimentally useful tool for manipulating alkyltransferase levels, it is necessary that the chosen formula I compound be active in vivo. Two separate Experiments were carried out to show Formula I compounds would be active in vivo. The two Experiments are as follows.

In Vivo Experiment I

In Experiment I, in vivo activity was tested by administering the drug $O^6$benzylquanine to CD-1 mice. Treatment by intraperitoneal injection at a dose of 10.2 mg/kg led to a more than 90% reduction in the alkyltransferase activity in the liver and kidney within 2h after injection (FIG. 5). The effect was then slowly reversed over the next 15h. However, when $O^6$-benzylguanine was given at a dose of 126 mg/kg (this required that the drug be dissolved in Cremophor EL, Sigma Chemical Co., St. Louis, Mo.) alkyltransferase activity was completely abolished for at least 16h.

In Vivo Experiment II

Male CD-1 mice (approx. 37g) and female LVG hamsters (approx. 100g) were purchased from Charles River Breeding Laboratories, Inc. (Wilmington, Mass). Female NIH Swiss, random-bred athymic mice were obtained from the Frederick Cancer Research and Development Center (Frederick, Md.). All animals were maintained under a controlled 12 h light-12 h dark cycle and allowed free access to water and food. Athymic mice were housed in isolated cubicles in a high efficiency particulate air filtered environment. All supplies were sterilized before passage into the facility.

Cell Cytotoxicity. Human glioma cells, SF767, were provided by Dr. M. E. Berens (Barrow Neurological Institute, Phoenix, Ariz.). SF767 are glial cells derived from a patient with astrocytoma. Berens et al., *Proc. Am. Assoc. Cancer Res.*, 31, 46 (1990). Cells were grown in Dulbecco's Modified Eagles Medium (DME) containing 10 mH Hepes buffer, penicillin (100 units/ml), streptomycin (100 µg/ml(, 1 mM sodium pyruvate, 10% fetal calf serum, and non-essential amino acids. Cell growth inhibition was analyzed using the MTT assay. Hansen et al., *J. Immunol. Methods*, 119, 203–210 (1989). Briefly, cells plated at a density of 500 cells/well in 96 well-plates were allowed to grow for 24 hours prior to the addition of $O^6$-benzylguanine such that the final concentration was 25 µM. Two hours later, increasing amounts of meCCNU were added for an additional 2h at which time medium was replaced with fresh medium and cells were allowed to grow for 4 days. At this time 20 µl of MTT solution (5mg/ml) was added followed 2h later by 100 µl lysing buffer (20% sodium dodecyl sulfate, 50% N,N-dimethylformamide, and 0.8% acetic acid, pH 4.5), and 22h after this the absorption at 570 nm was measured on a microplate reader and used to determine the cell number Hansen et al., ibid.

Drug Treatment. meCCNU (NSC 95441) was provided by the Drug Synthesis and Chemistry Branch, Division of Cancer Treatment, National Cancer Institute, Bethesda, Md. $O^6$-Methylguanine, $O^6$-benzylguanine, $O^6$-(p-methylbenzyl)guanine and 7-benzylguanine were synthesized as described. Dolan et al., *Cancer Res.*, 45, 6413–6417 (1985); Dolan et al., *Proc. Natl. Acad. Sci. USA*, 87, 5368–5372 (1990); Brookes et al., *J. Chem. Soc.* (c) 2026–2028, 1968.

[$^3$H]Methylnitrosourea (15.7 Ci/mmol) was purchased from Amersham. All other biochemicals were purchased through Sigma or Aldrich.

Mice treated with 10 mg $O^6$-benzylguanine/kg animal wt. were administered an intraperitoneal injection of 0.2 mg $O^6$-benzylguanine dissolved in 1 ml 0.85% (w/v) saline. In a separate experiment, mice were treated at a dose of 126 mg/kg by injection of 5 mg $O^6$-benzylguanine in 1 ml of 10% cremophor EL (Sigma) in 0.9% saline, pH 7.0. This was prepared by adding saline to the cremaphor containing drug, heating the solution to 37° C. for 30 min, followed by sonication for about 20 min. Hamsters were injected with 0.2 ml or 2 ml of the same solution such that the final dosage was 10 or 100 mg/kg. Solutions for the treatment of athymic mice (60 mg/kg final concentration) consisted of an intraperitoneal injection of 2 ml of a solution containing 0.67 mg of $O^6$-benzylguanine in 1 ml of 1% DMSO, 3% cremophor in 0.9% saline, pH 7.4. Animals treated with $O^6$-methylguanine in 10% cremophor/saline were administered 1.5 ml of 3.33 mg/ml to give a final dose of 126 mg/kg. At indicated times, animals were sacrificed by cervical dislocation and tissues were removed and frozen at $-80°$ C. until analysis. Crude extracts from tissues for alkyltransferase analysis were prepared as described previously, Domoradzki et al., *Carcinogenesis*, 5, 1641–1647 (1984).

Within 10–14 days after the injection of $5 \times 10^6$ SF767 cells into the flank region of NIH nude mice, tumors appeared. The animals were weighed and the tumors were measured with caliper every 48–72 hours. The tumor growth data are expressed as tumor volumes (mm$^3$), which is calculated from the equation length $\times$ width$^2 \times 0.5$. When tumors were in the range of 150–300 mm$^3$, athymic mice were randomized into four groups consisting of treatment with vehicle alone, $O^6$-benzylguanine alone, saline plus meCCNU or $O^6$-benzylguanine and meCCNU in combination. The meCCNU was dissolved in 10% ethanol/9% cremophor/81% saline (v/v) and was given i.p. 1h following $O^6$-benzylguanine. Solutions were in a volume of 0.01 ml/g animal weight to give a final dosage of 7.5 or 15 mg/kg animal wt. Tumor measurements and animal weights were determined 3 times per week.

Alkyltransferase Activity. Alkyltransferase activity was measured as removal of [$^3$H] $O^6$-methylguanine from a [$^3$H] methylated DNA substrate as described Dolan et al., *Proc. Natl. Acad. Sci. USA* 87:5368–5372 (1990); Domoradzhi et al., *Carcinogenesis*, 5, 1641–1647 (1984). After incubation of the methylated DNA with extract, the DNA was acid-hydrolyzed and modified bases were separated on a reverse-phase column eluted with 7.5% methanol in 0.5M ammonium formate, pH 4.2 as described previously, Dolan et al., *Cancer Research* 46, 4500–4504 (1986).

Alkyltransferase activity levels were determined in extracts prepared from lung, spleen, esophagus, kidney and liver of CD-1 mice four hours after an intraperitoneal injection of 126 mg/kg $O^6$-methylguanine, 126 mg/kg $O^6$-benzylguanine, or vehicle alone, Table 2.

As indicated, except for the esophagus (70% reduction), the activity was decreased by only 35 to 50% after treatment with $O^6$-methylguanine while $O^6$-benzylguanine treatment led to almost complete loss of activity. The extent of depletion in alklytransferase activity in mouse liver with $O^6$-methylguanine is consistent with previous data from our laboratory Dolan et al., *Cancer Chemother. Pharmacol.*, 25, 103–108 (1989).

TABLE 2

Effect of $O^6$-alkylguanine on alkyltransferase levels in mouse tissues.

| Tissue | Alkyltransferase activity (% Control) in mice treated with | | |
|---|---|---|---|
| | No drug* | $O^6$-methylguanine | $O^6$-benzylguanine |
| Lung | 100 | 54 ± 17 | 2 ± 3 |
| Spleen | 100 | 65 ± 8 | 12 ± 11 |

TABLE 2-continued

Effect of $O^6$-alkylguanine on alkyltransferase levels in mouse tissues.

| Tissue | Alkyltransferase activity (% Control) in mice treated with | | |
|---|---|---|---|
| | No drug* | $O^6$-methylguanine | $O^6$-benzylguanine |
| Esophagus | 100 | 30 ± 9 | 0 |
| Kidney | 100 | 56 ± 13 | 0 |
| Liver | 100 | 53 ± 6 | 1 ± 1 |

*The absolute values for the control alkyltransferase activity in fmol/mg protein were lung, 42; spleen, 64; esophagus, 18; kidney, 16; and liver, 30.

Figure 6A:
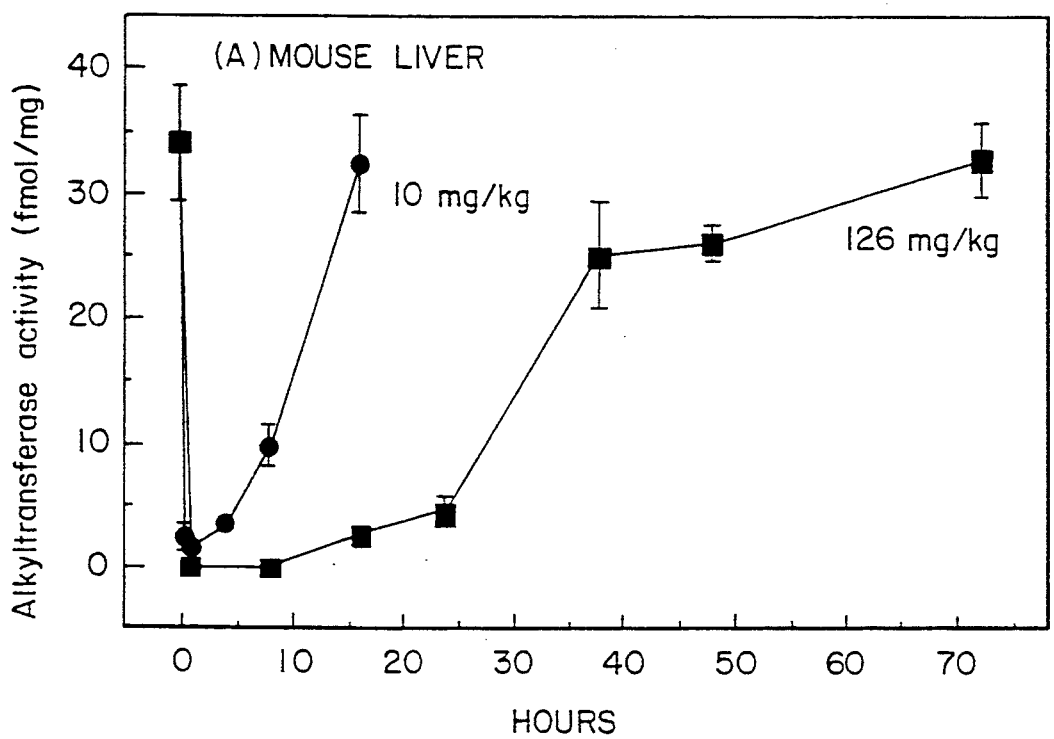
FIG. 6(A) and 6(B) show depletion of alkyltransferase in mouse liver and kidney by administration of $O^6$-benzylguanine. CD-1 mice (approx. 37g) treated with 10 mg/kg (●) were given two intraperitoneal injections of 1 ml saline containing 0.2 mg/kg $O^6$-benzylguanine or saline alone and those treated with 126 mg/kg (■) were given one injection of 10% cremophor/saline containing 5 mg/ml $O^6$-benzylguanine or vehicle alone. The mice were killed at the time shown and the alkyltransferase activity was determined in liver (A) or kidney (B). The means of S.D. for estimations on at least three mice which were each assayed in duplicate are shown.
Figure 6B:
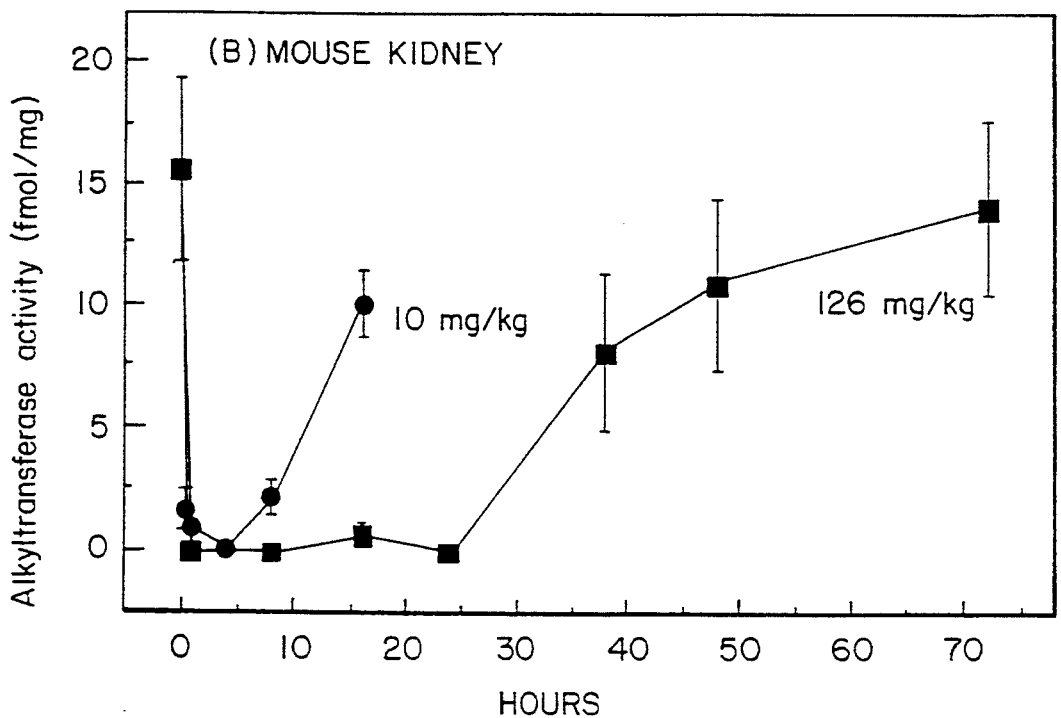

When $O^6$-benzylguanine was administered to CD-1 mice at a dose of 10 or 126 mg/kg, there was a rapid decrease in the level of active alkyltransferase in both liver and kidney (FIG. 6(a) and 6(B)). The recovery in the liver to basal levels required 16h for mice treated at the low dose and more than 36h for mice treated at the higher dose of $O^6$-benzylguanine. There was no effect of saline alone or cremophor/saline (used as a vehicle for the higher doses) on tissue alkyltransferase levels. $O^6$-Benzylguanine and $O^6$-(p-methylbenzyl)guanine at a dose of 4.9 mg/kg reduced alkyltransferase levels in liver and kidney to 35% and 54% basal levels at 1 hour after injection, respectively, yet 7-benzylguanine (2.5 mg/kg) had no effect on alkyltransferase levels (data not shown).

Figure 7A:
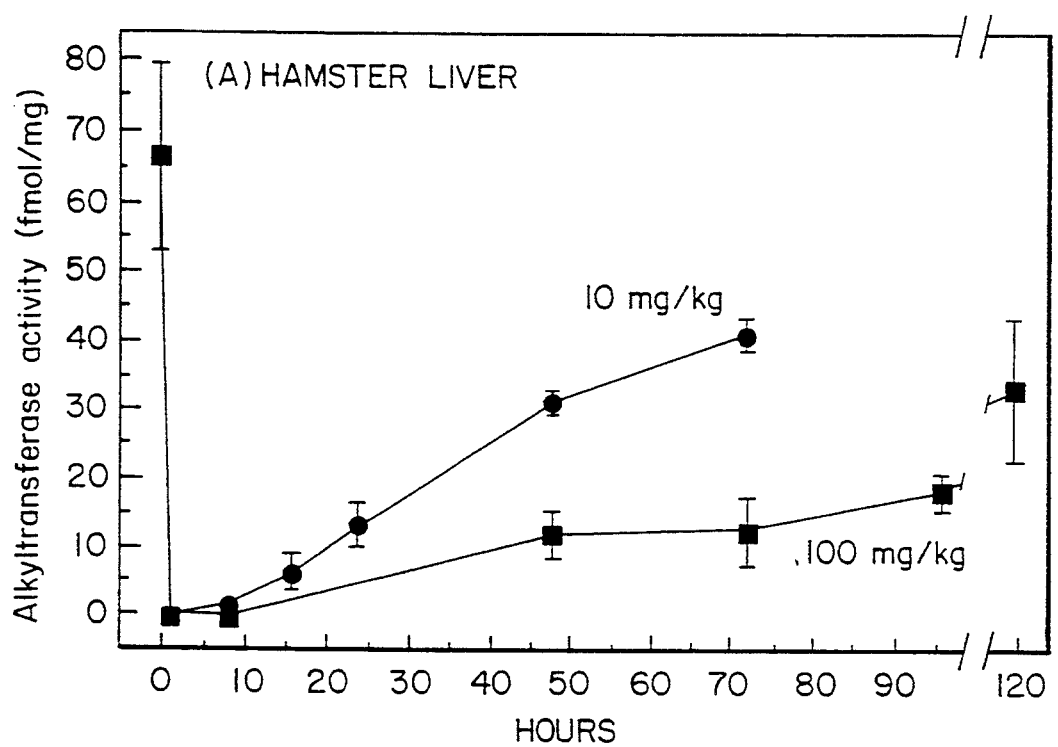
FIGS. 7(A) and 7(B) show depletion of alkyltransferase in hamster liver and kidney by administration of $O^6$-benzylguanine. LVG hamsters (approx. 100g) treated with 10 mg/kg (●) or 100 mg/kg (●) were given either 0.2 ml or 2 ml, respectively, of 10% cremophor/saline containing 5 mg $O^6$-benzylguanine/ml or vehicle alone. The animals were killed at the time indicated and the alkyltransferase activity was determined in liver (A) or kidney (B). The means and S.D. for estimations on at least three hamsters which were each assayed in duplicate are shown.
Figure 7B:
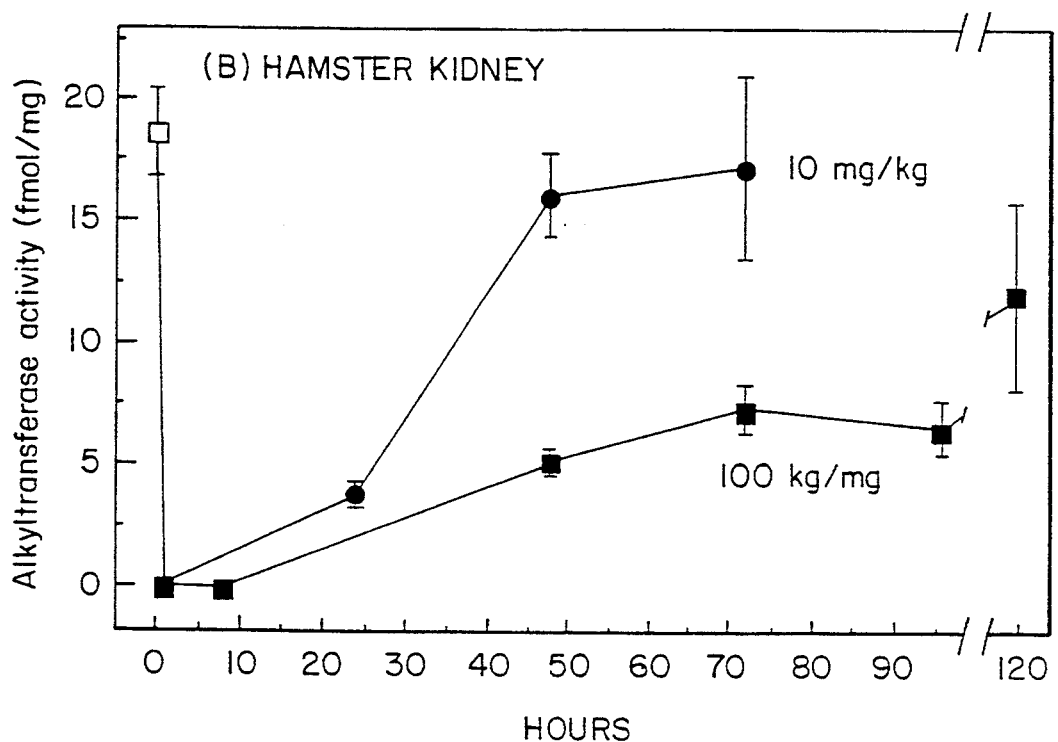

Alkyltransferase activity dropped to undetectable levels in tissues of hamsters receiving an intraperitoneal injection of 10 or 100 mg $O^6$-benzylguanine/kg (FIG. 7(A) and 7(B)). The return to normal levels was much slower than for mouse tissues with levels in the liver reaching 50% basal level at 48h following treatment with 10 mg/kg and at 120h after treatment with 100 mg/kg. The alkyltransferase levels in the hamster kidney had returned to only 35% of basal levels at 96h after injection of 100 mg/kg.

Figure 8:
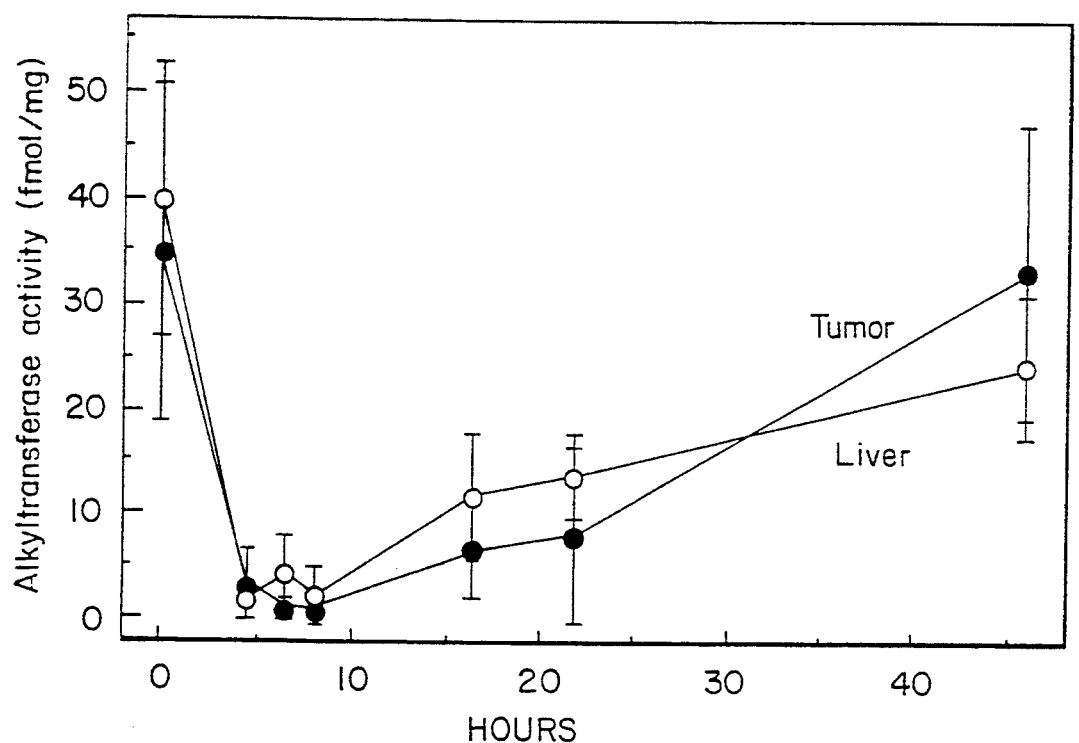
FIG. 8 shows alkyltransferase depletion in livers (○) and SF767 xenograft tumors (●) carried in nude mice after treatment with 60 mg/kg $O^6$-benzylguanine. Animals were sacrificed at various time intervals post-injection as indicated, tumors were excised, and alkyltransferase activity was analyzed as described.

A human glioma (SF767) was grown in nude mice injected in the flank region with $5 \times 10^6$ cells. Three weeks later, animals with tumor sizes in the range of $229 \pm 117$ mm$^3$ were injected with 60 mg $O^6$-benzylguanine/kg and randomized into groups to be killed at various times up to 46h. Alkyltransferase activity was then determined in the tumor and livers from these animals (FIG. 8). The activity in the liver and tumors remained low for up to 8h after $O^6$-benzylguanine exposure and rose slowly to basal levels over the next 38 hours (FIG. 8).

Figure 9:
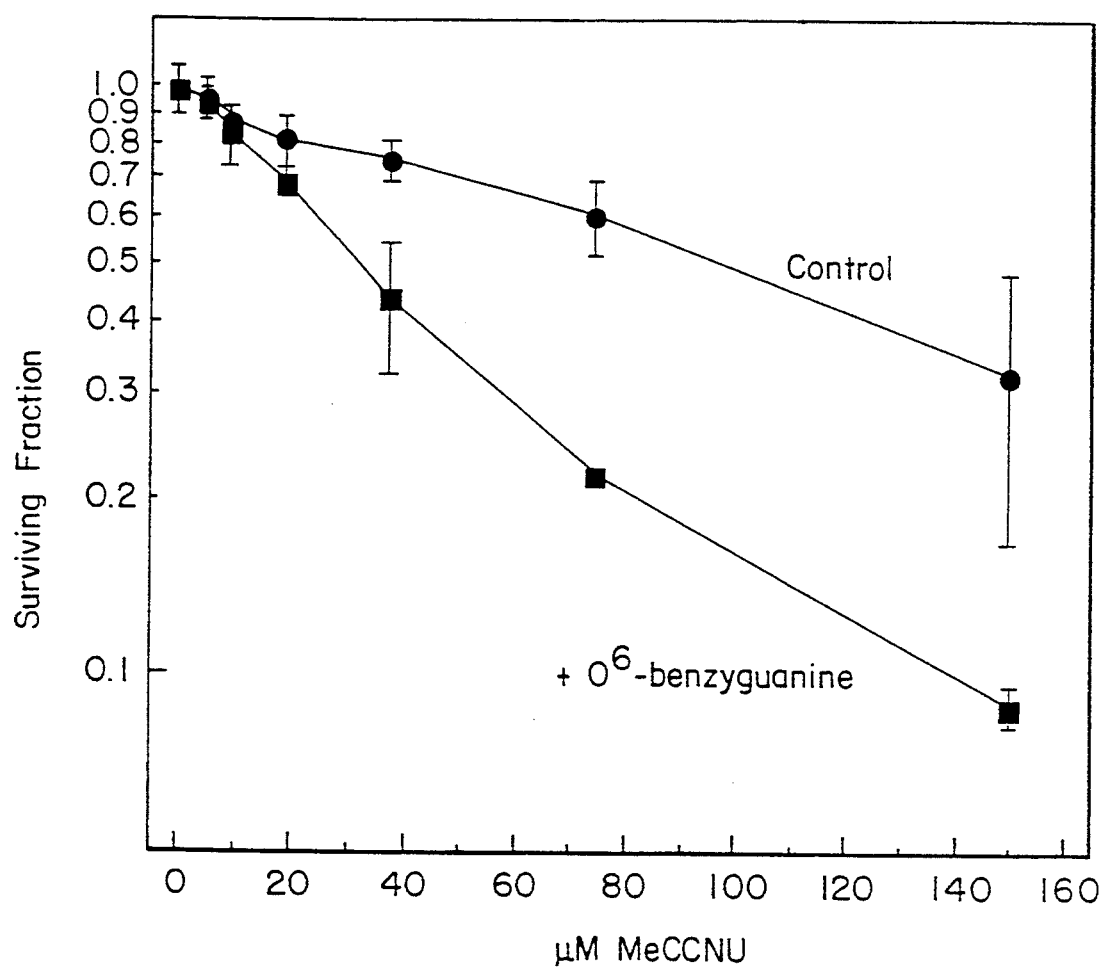
FIG. 9 shows the effect of $O^6$-benzylguanine (b⁶G) on proliferation of SF767 cells treated with meCCNU. SF767 cells were exposed to fresh medium (●) or medium containing 10μM $O^6$-benzylguanine (■) for 2h prior to treatment with meCCNU for 2h at the concentrations indicated. The MTT cytotoxicity assay was performed to determine the cell growth 5 days post treatment.

The effect of $O^6$-benzylguanine on the sensitivity of the SF767 cells grown in culture to meCCNU is illustrated in FIG. 9. There was a 3.8 fold decrease in the ED$_{50}$ upon incubation with 10 μM $O^6$-benzylguanine for 2 hours prior to meCCNU exposure. $O^6$-Benzylguanine alone had no effect on cell growth.

Figure 10C:
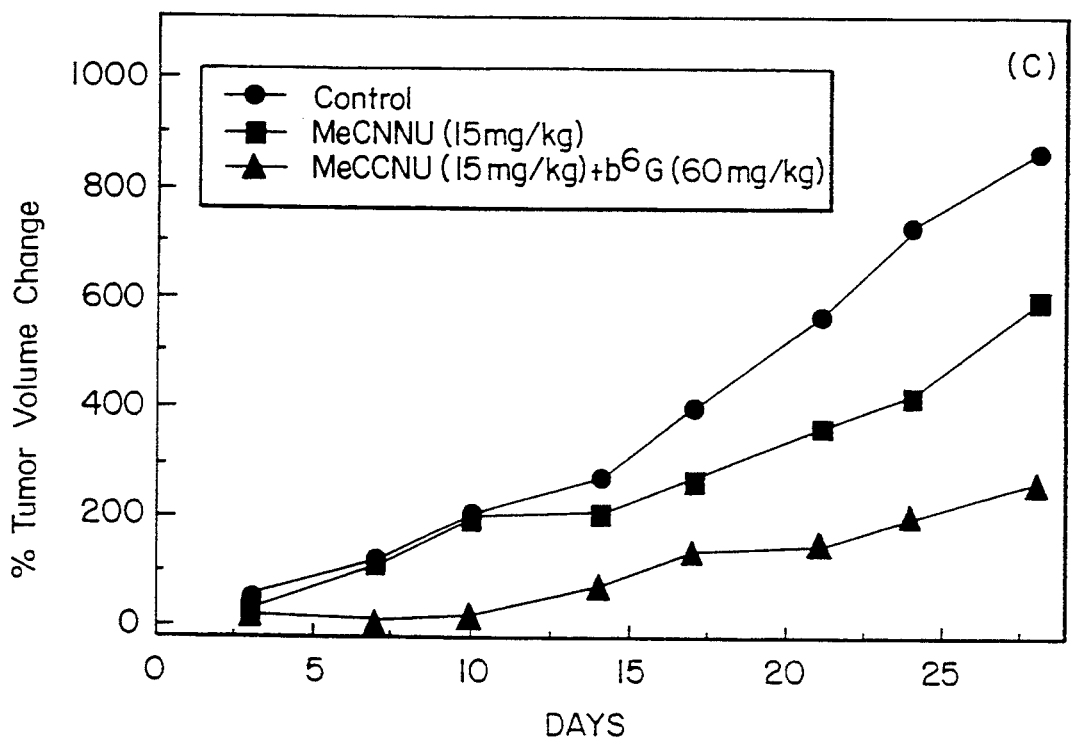
FIGS. 10(A) and 10(B) and 10(C) shows the response of the SF767 tumor carried in athymic mice to vehicle alone or $O^6$-benzylguanine and/or meCCNU. 10 (A); Results for relative tumor volumes in athymic mice carrying SF767 tumors treated with vehicle (●) or $O^6$-benzylguanine (○). 10(B); Results for relative tumor volumes after treatment with vehicle (●), 7.5 mg/kg meCCNU (■) or $O^6$-benzylguanine plus 7.5 mg/kg meCCNU (▲). 10(C); Results for relative tumor volume after treatment with vehicle (●), 15 mg/kg meCCNU (■) or $O^6$-benzylguanine plus 15 mg/kg meCCNU (▲).
Figure 10:
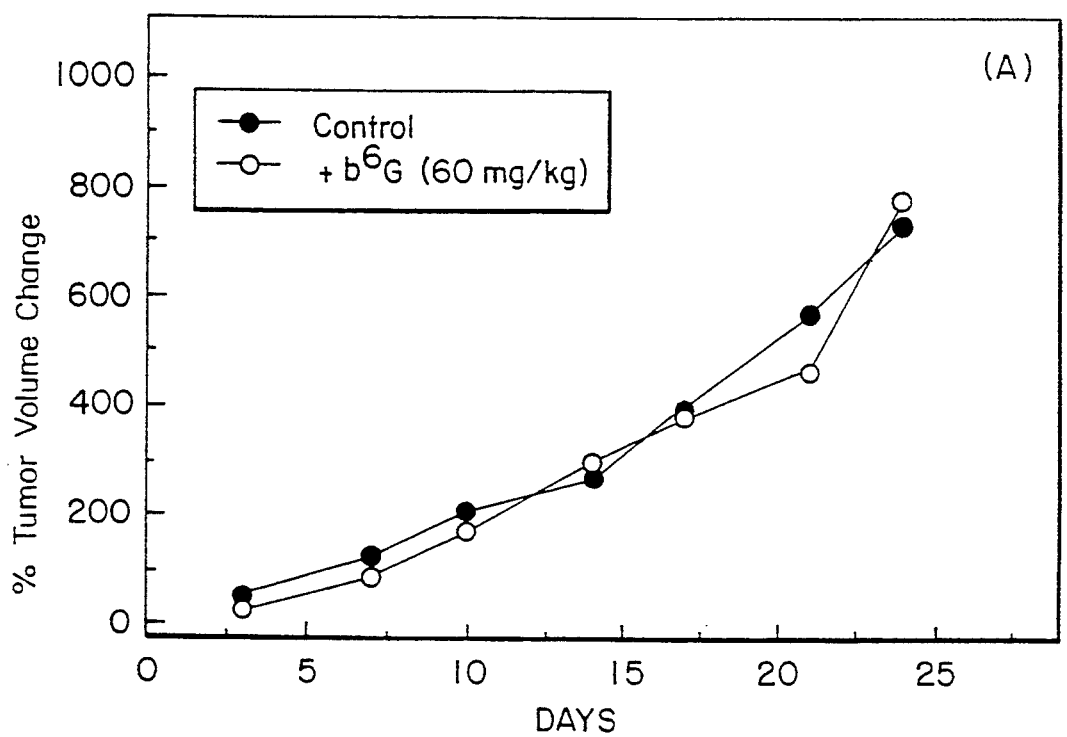
Figure 10B:
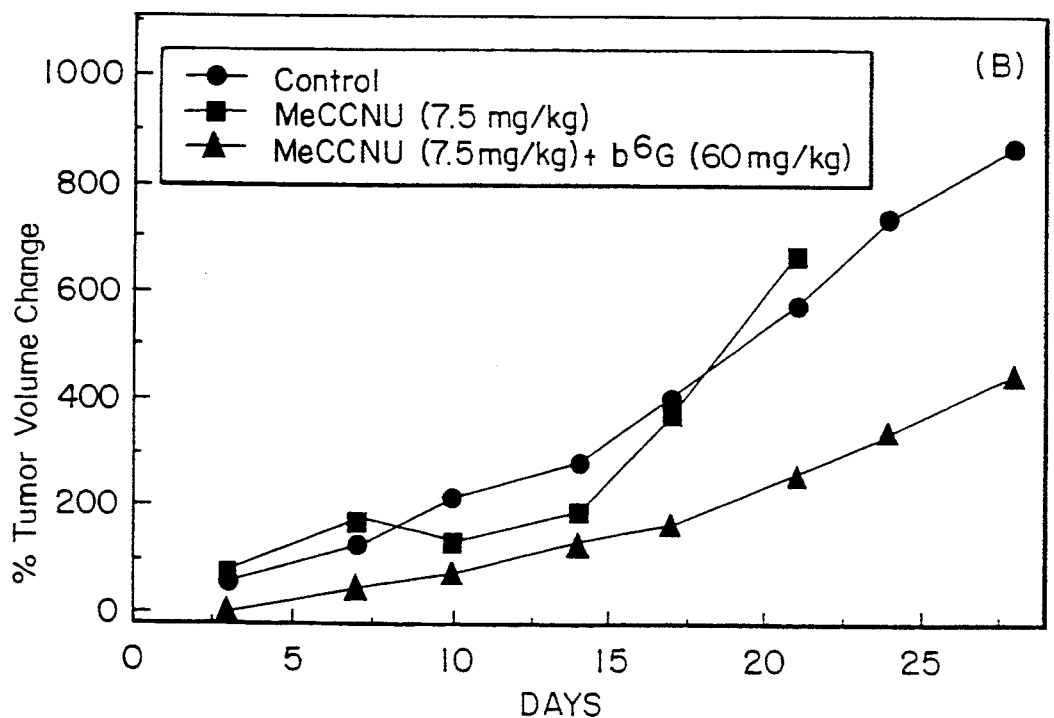

The growth rate of SF767 tumor xenografts was determined in mice treated with vehicle alone, $O^6$-benzylguanine (60 mg/kg) alone, meCCNU (7.5 and 15 mg/kg), and the combination of $O^6$-benzylguanine and meCCNU (FIG. 10(A) and 10(B)). Tumor growth rate was unaffected by $O^6$-benzylguanine alone or the lower dose of meCCNU alone (FIG. 10(A) and 10(B)) However, on day 21 and thereafter, the average size of tumors treated with $O^6$-benzylguanine and meCCNU (7.5 mg/kg) was 2.6 fold smaller than those treated with meCCNU alone (FIG. 10(B)). FIG. 10(C) illustrates that at the higher dose of meCCNU alone, tumor growth was inhibited but a much greater effect was obtained in response to the combination of $O^6$-benzylguanine treatment followed by meCCNU. As indicated in FIG. 10(C), on day 21, tumors of control animals were 1.6 fold greater in volume than those in meCCNU treated animals and 3.7 fold larger than animals treated with both $O^6$-benzylguanine and meCCNU.

As shown in FIGS. 10(B) and 10(C), there was a marked difference in tumor size between the untreated control mice and the mice treated with the combination of $O^6$-benzylguanine and meCCNU at all times. A summary of percentage tumor volume data at the later time points is given in Table 3. On day 24, the tumor size in mice treated with $O^6$-benzylguanine in addition to either dose of meCCNU was statistically different than the controls and 4 days later the difference in the group treated with $O^6$-benzylguanine and 15 mg/kg of meCCNU was statistically significant. There was no obvious sign of increased toxicity as a result of the combination of $O^6$-benzylguanine with meCCNU. One animal treated with 15 mg/kg meCCNU and $O^6$-benzylguanine died of gastric ulcer from bacterial origin. Other animals in this group lost an average of 16% body weight. However, they regained the weight within approximately 1–2 weeks.

TABLE 3

Effect of $O^6$-benzylguanine and meCCNU on SF767 tumor growth.

| Treatment | % Tumor volume change at day indicated | |
|---|---|---|
| | Day 24 | Day 28 |
| Control | 736 ± 317 | 868 ± 471 |
| meCCNU (7.5 mg/kg) | 447 ± 65 | 666 ± 228 |
| meCCNU (7.5 mg/kg) + $O^6$-benzylguanine | 337 ± 101$^a$ | 444 ± 132 |
| meCCNU (15 mg/kg) | 424 ± 257 | 602 ± 435 |
| meCCNU (15 mg/kg) + $O^6$-benzylguanine | 207 ± 96$^a$ | 270 ± 161$^a$ |

$^a$Significantly different from Control; $p \leq 0.05$ from student t-test

The above Examples and In Vivo Experiments I and II demonstrate that $O^6$-benzylguanines and other compounds encompassed by Formula I, might be more effective at depleting alkyltransferase levels than any other agents studied so far. All of the $O^6$-benzylguanine derivatives and $O^6$-benzyl-2'-deoxyguanosine derivatives tested were much more active than $O^6$-methylguanine or other derivatives such as $O^6$-n-butylguanine in terms of concentration needed to inactivate as well as the rate and completeness of alkyltransferase inactivation. For example, even at low doses of the order of 10 mg/kg, $O^6$-benzylguanine completely depleted the alkyltransferase activity in mouse liver and kidneys. Although larger doses were required to achieve longer lasting reductions, it should be noted that a transient decrease is all that is needed to enhance the effectiveness of chloroethylating agents. Furthermore, there were no obvious toxic effects of much larger doses which led to a long lasting reduction in alkyltransferase levels. Treatment with $O^6$-benzylguanine and other compounds encompassed hereby, may also be a useful way in which to evaluate the role of the alkyltransferase activity in protection against the mutagenic and carcinogenic actions of alkylating agents.

The $O^6$-benzylguanine, guanosine and 2'-deoxyguanosine derivatives employed in the present invention may be made into pharmaceutical compositions by accommodation with appropriate pharmaceutically acceptable excipients or carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. The following methods and excipients are merely exemplary and are in no way limiting.

In pharmaceutical dosage forms, the $O^6$-benzylguanine, guanosine and $2'$-deoxyguanosine derivatives employed in the present invention may be used in the form of their pharmaceutically acceptable salts, and also may be used alone or in appropriate association, as well as in combination with other pharmaceutically active compounds.

In the case of oral preparations, the $O^6$-benzylguanine derivatives of the present invention may be used alone or in combination with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and, if desired, with diluents, buffering agents, moistening agents, preservatives and flavoring agents.

Furthermore, the $O^6$-benzylguanine derivatives employed in the present invention may be made into suppositories by mixing with a variety of bases such as emulsifying bases or water-soluble bases.

The $O^6$-benzylguanine derivatives employed in the present invention also may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the $O^6$-benzylguanine derivatives employed in the present invention in the form of a liquid or minute powder may be filled up in an aerosol container with gas or liquid spraying agents, and if desired, together with conventional adjuvants such as humidifying agents. They may also be formulated as pharmaceuticals for non-pressured preparations such as a nebulizer or an atomizer.

The amount of $O^6$-benzylguanine; guanosine or $2'$-deoxyguanosine derivative employed in the present invention to be used varies according to the degree of the effective amount required for treating tumor cells. A suitable dosage is that which will result in a concentration of the $O^6$-benzylguanine, guanosine or $2'$-deoxyguanosine derivative in the tumor cells to be treated which results in the depletion of AGT activity, e.g. about 1–2000 mg/kg prior to chemotherapy and preferably 10–800 mg/kg prior to chemotherapy.

Unit dosage forms for oral administration such as syrups, elixirs, and suspensions wherein each dosage unit (e.g., teaspoonful or tablespoonful) contains a predetermined amount of an $O^6$-benzylguanine derivative employed in the present invention can be combined with a pharmaceutically acceptable carrier, such as Sterile Water for Injection, USP, or normal saline.

The guanine $O^6$-benzylguanine derivatives employed in the present invention also can be administered rectally via a suppository. The suppository can include vehicles such as cocoa butter, carbowaxes and polyethylene glycols, which melt at body temperature, yet are solidified at room temperature. transdermally in an appropriate vehicle or salt or converted to a salt. Adsorption may be aided by the use of an electric current or field.

The $O^6$-benzylguanine derivatives employed in the present invention also may be administered with an appropriate vehicle for buccal or sublingual administration, if so desired.

The $O^6$-benzylguanine derivatives employed in the present invention also can be utilized in aerosol formulations to be administered via inhalation. The $O^6$-benzylguanine derivatives can be formulated into pressurized acceptable propellants such as dichlorodifluoromethane, propane, nitrogen and the like.

The term "unit dosage form" as used herein generally refers to physically discrete units suitable as unitary dosages for human and animal subjects, each unit containing a predetermined quantity of at least one $O^6$-benzylguanine derivative encompassed by Formula I, calculated in an amount sufficient to produce the desired effect in association with a pharmaceutically acceptable diluent, carrier, excipient or vehicle. The specifications for the novel unit dosage forms of the present invention depend on the particular compound employed and the effect to be achieved, and the pharmacodynamics associated with each compound in the host.

The pharmaceutically acceptable excipients, for example, vehicles, adjuvants, carriers or diluents are readily available to the public.

Any necessary adjustments in dose can be readily made to meet the chemotherapeutic treatment requirements and adjusted accordingly by the skilled practitioner.

Alkylating agents, such as chloroethylating agents, may be administered using conventional techniques such as those described in Wasserman et al, *Cancer*, 36: pp. 1258–1268 (1975); and *Physicians' Desk Reference*, 44th ed., Edward R. Barnhart publisher (1990). For example, 1,3-bis(2-chloroethyl)-1-nitrosourea (carmustine or BCNU, Bristol-Myers, Evansville, Ind.) may be administered intravenously at a dosage of from about 150 to 200 mg/m$^2$ every six weeks. Another alkylating agent, 1-(2-chloroethyl)-3-cyclohexyl-1-nitrosourea (lomustine or CCNU, BristolMyers), may be administered orally at a dosage of about 130 mg/m$^2$ every six weeks. Other alkylating agents may be administered in appropriate dosages via appropriate routes of administration known to skilled medical practioners.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical composition which comprises compounds of the formula,

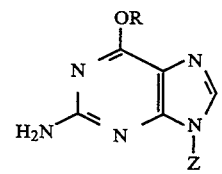

wherein Z is

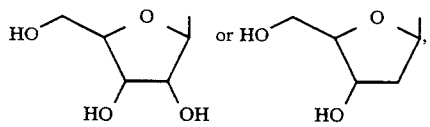

and R is a benzyl group or a substituted benzyl group substituted at the ortho, meta or para position with a substituent selected from the group consisting of halogen, nitro, phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, and $SO_nR_1$ wherein n is 0, 1, 2 or 3 and $R_1$ is hydrogen, alkyl of 1–4 carbon atoms, or phenyl; and a pharmaceutically acceptable excipient.

2. The composition of claim 1, wherein R is a benzyl group.

3. The composition of claim 1, wherein R is a p-chlorobenzyl group or a p-fluorobenzyl group.

4. The composition of claim 1, wherein R is a p-methylbenzyl group.

5. The composition of claim 1, further comprising an anti-neoplastic alkylating agent.

6. The composition of claim 2, further comprising an anti-neoplastic alkylating agent.

7. The composition of claim 3, further comprising an anti-neoplastic alkylating agent.

8. The composition of claim , further comprising an anti-neoplastic alkylating agent.

9. The pharmaceutical composition of claim 1, wherein Z is

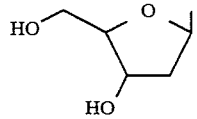

and R is a benzyl group or a substituted benzyl group substituted with a substituent selected from the group consisting of halogen, nitro, alkyl of 1–4 carbon atoms, alkoxy of 1–4 carbon atoms, trifluoromethyl and hydroxymethyl.

10. The pharmaceutical composition of claim 9, further comprising an anti-neoplastic alkylating agent.

* * * * *

UNITED STATES PATENT AND TRADEMARK OFFICE
CERTIFICATE OF CORRECTION

| | | |
|---|---|---|
| PATENT NO. | : 5,352,669 | |
| APPLICATION NO. | : 07/616913 | |
| DATED | : October 4, 1994 | |
| INVENTOR(S) | : Moschel et al. | |

It is certified that error appears in the above-identified patent and that said Letters Patent is hereby corrected as shown below:

IN THE TITLE PAGE:

Item (73) Assignees: "The United States of America as represented by the Department of Health and Human Services, Washington, DC (US)" should read --The Government of the United States of America as represented by the Secretary, Department of Health and Human Services, Rockville, MD (US); The Penn State Research Foundation, University Park, PA--.

At column 1, line 12 immediately before "FIELD OF INVENTION," please add the following statement:

--STATEMENT REGARDING
FEDERALLY SPONSORED RESEARCH AND DEVELOPMENT

This invention was also made with Government support under Grant Number CA18137 and CA47728 awarded by the National Cancer Institute of the National Institutes of Health. The Government has certain rights in this invention.--

Signed and Sealed this

Seventeenth Day of April, 2007

JON W. DUDAS
*Director of the United States Patent and Trademark Office*